United States Patent
Yoshikawa et al.

(10) Patent No.: US 11,391,687 B2
(45) Date of Patent: Jul. 19, 2022

(54) GAS SENSOR DEVICE AND METHOD FOR REMOVING GAS COMPONENT

(71) Applicants: NATIONAL INSTITUTE FOR MATERIALS SCIENCE, Ibaraki (JP); KYOCERA CORPORATION, Kyoto (JP)

(72) Inventors: Genki Yoshikawa, Ibaraki (JP); Kota Shiba, Ibaraki (JP); Gaku Imamura, Ibaraki (JP); Takanori Yasuda, Kyoto (JP); Kyohei Kobayashi, Kyoto (JP); Hisashi Sakai, Kyoto (JP)

(73) Assignees: NATIONAL INSTITUTE FOR MATERIALS SCIENCE, Ibaraki (JP); KYOCERA CORPORATION, Kyoto (JP)

( * ) Notice: Subject to any disclaimer, the term of this patent is extended or adjusted under 35 U.S.C. 154(b) by 557 days.

(21) Appl. No.: 16/342,268

(22) PCT Filed: Oct. 24, 2017

(86) PCT No.: PCT/JP2017/038256
§ 371 (c)(1),
(2) Date: Apr. 16, 2019

(87) PCT Pub. No.: WO2018/079509
PCT Pub. Date: May 3, 2018

(65) Prior Publication Data
US 2019/0323982 A1    Oct. 24, 2019

(30) Foreign Application Priority Data
Oct. 27, 2016  (JP) .............................. JP2016-210632

(51) Int. Cl.
*G01N 27/22*    (2006.01)
*G01N 33/00*    (2006.01)

(52) U.S. Cl.
CPC ......... *G01N 27/22* (2013.01); *G01N 33/0029* (2013.01); *G01N 33/0031* (2013.01);
(Continued)

(58) Field of Classification Search
None
See application file for complete search history.

(56) References Cited

U.S. PATENT DOCUMENTS 6,431,016 B1 *   8/2002   Payne ................ G01N 33/0006
                                                                73/23.34
2013/0133433 A1   5/2013   Yoshikawa et al.
(Continued)

FOREIGN PATENT DOCUMENTS

EP    2 762 856    8/2014
EP    3 208 597    8/2017
(Continued)

OTHER PUBLICATIONS

Communication pursuant to Article 94(3) EPC dated Sep. 15, 2021 in corresponding European Patent Application No. 17 863 461.4.
(Continued)

*Primary Examiner* — Daniel S Larkin
(74) *Attorney, Agent, or Firm* — Wenderoth, Lind & Ponack, L.L.P.

(57) ABSTRACT

The invention provides: a gas sensor device that is capable of removing a component adsorbed on a gas sensor by relatively simple means and easily restoring a signal baseline of the gas sensor to a constant state; and a method for removing a gas component. The gas sensor device according to an embodiment of the invention includes a gas sensor and cleaning means that contains a liquid for cleaning the gas sensor. The gas sensor includes a sensor main body that is capable of detecting a characteristic parameter of a component present in a gas phase or a liquid phase, and a sensitive
(Continued)

membrane that is coated on a surface of the sensor main body and is durable against the liquid.

6 Claims, 5 Drawing Sheets

(52) U.S. Cl.
CPC .................. *G01N 2291/021* (2013.01); *G01N 2291/0256* (2013.01)

(56) References Cited

U.S. PATENT DOCUMENTS

| | | |
|---|---|---|
| 2013/0171687 A1 | 7/2013 | Moularat et al. |
| 2016/0103108 A1* | 4/2016 | Yi .................. G01N 29/036 436/501 |

FOREIGN PATENT DOCUMENTS

| | | |
|---|---|---|
| JP | 7-174728 | 7/1995 |
| JP | 2014-219223 | 11/2014 |
| WO | 2011/148774 | 12/2011 |
| WO | 2016/121155 | 8/2016 |

OTHER PUBLICATIONS

Email from European Examiner dated Sep. 17, 2021, providing missing portion from Communication cited in CA above in EP 17 863 461.4.

International Search Report dated Jan. 23, 2018 in International Application No. PCT/JP2017/038256.

D. Lee, S. Kim, I. Chae, S. Jeon, and T. Thundat, "Nanowell-patterned TiO2 microcantilevers for calorimetric chemical sensing," Applied Physics Letters 104, 141903 (2014).

G. Yoshikawa, T. Akiyama, S. Gautsch, P. Vettiger, and H. Rohrer, "Nanomechanical Membrane-type Surface Stress Sensor," Nano Letters 11, 1044-1048 (2011).

K. Shiba, T. Sugiyama, T. Takei, and G. Yoshikawa, "Controlled growth of silica-titania hybrid functional nanoparticles through a multistep microfluidic approach," Chem. Commun. 51, 15854-15857 (2015).

Office Action dated Jun. 4, 2021 in corresponding Chinese Patent Application No. 201780066524.2, with English Translation.

Extended European Search Report dated Jun. 18, 2020 in corresponding European Patent Application No. 17863461.4.

Office Action dated Mar. 11, 2021 in corresponding European Patent Application No. 17 863 461.4.

Notification of Reasons for Refusal dated Jun. 2, 2020 in corresponding Japanese Patent Application No. 2018-547668, with English Translation.

Office Action dated Dec. 22, 2021 in corresponding Chinese Patent Application No. 201780066524.2, with English Translation.

Office Action dated Apr. 22, 2022 in corresponding Chinese Patent Application No. 201780066524.2, with English Translation.

* cited by examiner

GAS SENSOR DEVICE AND METHOD FOR REMOVING GAS COMPONENT

TECHNICAL FIELD

The present invention relates to a gas sensor device and a method for removing a gas component.

BACKGROUND ART

Identification of a mixed gas consisting of a plurality of components is an important issue in various applications ranging from the medical care to various industries. Hence, a gas sensor for detecting a component contained in the mixed gas has previously been known.

In general, in a case where pattern recognition is performed by using a gas sensor, sensor signals in response to various standard samples are obtained in advance, and a signal obtained from an unknown sample is evaluated with the sensor signals, and thereby the sample is identified.

In this case, reproducibility of the sensor signal is very important; however, the mixed gas which will be the sample often contains a wide variety of components. For example, it is said that a scent of coffee contains 500 or more kinds of various components, and exhaled breath contains 1,000 or more kinds of various components.

Hence, a gas containing such various components can contain a component that does not desorb or takes a long time to desorb once adsorbed to a sensor element of a gas sensor. This will not only cause a change of the baseline of the signal of the sensor but also have an impact on the results of the upcoming measurement, making the strict reproducibility difficult to assure.

To deal with such a problem, there have been reported such attempts as a method of heating a sensor element, and a method of using a photocatalytic material in a sensitive membrane (for example, Non Patent Literature 1).

SUMMARY OF INVENTION

Technical Problem

However, in the case of the prior method such as Non Patent Literature 1, it is not possible to easily perform the method because the method involves modification of the sensor element or the sensitive membrane, and a problem arises in that it is not easy to restore the baseline of the signal of the gas sensor to a constant state.

The invention is made with consideration for circumstances described above, and an object thereof is to provide a gas sensor device, which is capable of removing a component attached to a gas sensor by relatively simple means and easily restoring a signal value which is a baseline of the gas sensor to a constant state, and a method for removing a gas component.

Solution to Problem

In order to solve the above-described problem, the invention provides a gas sensor device including a gas sensor, and cleaning means that contains liquid for cleaning the gas sensor, in which the gas sensor includes a sensor main body that is capable of detecting a characteristic parameter of a component present in a gas phase or a liquid phase, and a sensitive membrane coated on a surface of the sensor main body and is durable against the liquid.

In the gas sensor device, the sensitive membrane is preferably formed with fine particles having a grain size of 1 nm to 1 mm.

The invention provides a method for removing a gas component adsorbing on a gas sensor with a liquid, wherein the gas sensor comprises a sensor main body that is capable of detecting a characteristic parameter of a component present in a gas phase or a liquid phase, and a sensitive membrane coated on a surface of the sensor main body and is durable against the liquid, the method including: (1) a cleaning step of causing the gas sensor and the liquid to be brought into contact with each other; and (2) a drying step of drying the gas sensor in a gas phase after the cleaning step.

In the method for removing a gas component, in (2) the drying step, a signal detected by the sensor main body due to a characteristic parameter based on a component in the gas phase preferably converges to a constant value.

In the method for removing a gas component, (1) the cleaning step, preferably includes steps of calculating a reference value in a liquid phase state based on a signal of the characteristic parameter detected by the sensor main body due to a component in a liquid phase, and adjusting the sensor main body based on the reference value in the liquid phase state.

In the method for removing a gas component, the step of adjusting the sensor main body preferably includes a step of comparing the reference value of the cleaning step with a convergence value of the drying step and improving reproducibility of a sensor signal.

In the method for removing a gas component, the step of improving the reproducibility of the sensor signal preferably includes a step of adjusting at least one selected from the group consisting of detection sensitivity, an offset, and a response signal of the sensor based on a result of the comparison.

Advantageous Effects of Invention

According to a gas sensor device and a method for removing a gas component of the invention, it is possible to remove a component adsorbed on a gas sensor by relatively simple means, it is easy to restore a signal value (offset from a predetermined level of 0 V or the like) which is a baseline of the gas sensor to a constant state, and thus it is possible to reliably secure reproducibility of a measurement result.

DESCRIPTION OF EMBODIMENTS

Figure 1:
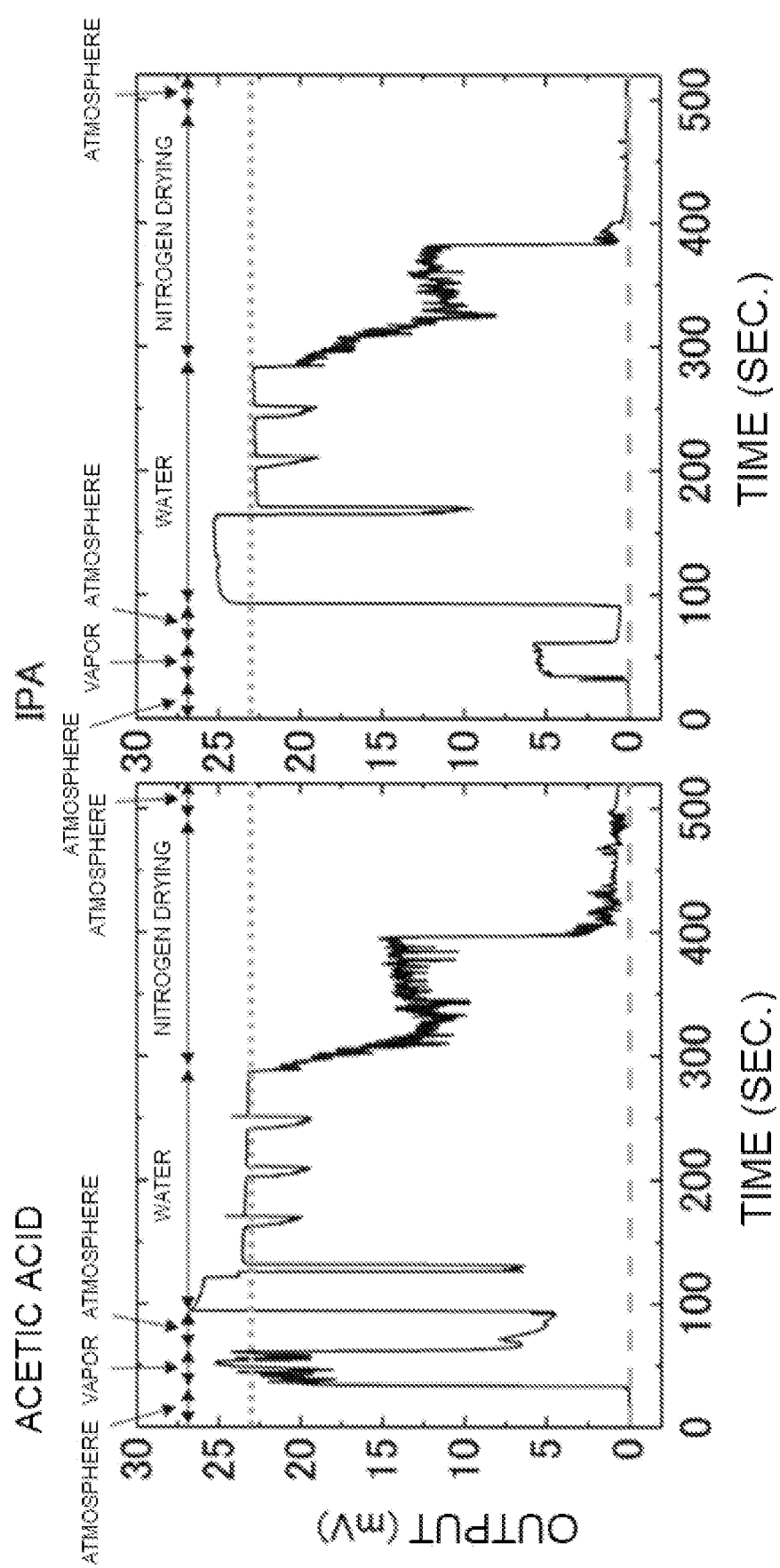
FIG. 1 is a graph showing a sensor signal measured when acetic acid vapor and isopropyl alcohol (IPA) vapor are exposed to a Membrane-type Surface stress Sensor (MSS), which is coated with a sensitive membrane that is durable against liquid water, (Non Patent Literature 2), and then the MSS is immersed in the liquid water, is dried in nitrogen, and remains in the atmosphere, thereby being restored to a steady-state. A graph shape (response signal) in a period of time during which the MSS is immersed in the liquid water in the graph of FIG. 1 has a blunt saw-teeth waveform. This is because, instead of continuously holding the MSS in the same water in the period of time, an operation of holding the MSS in the water for a certain time and, then, moving the MSS to other fresh water, and holding the MSS in the fresh water for about the same time is repeated.
Figure 2:
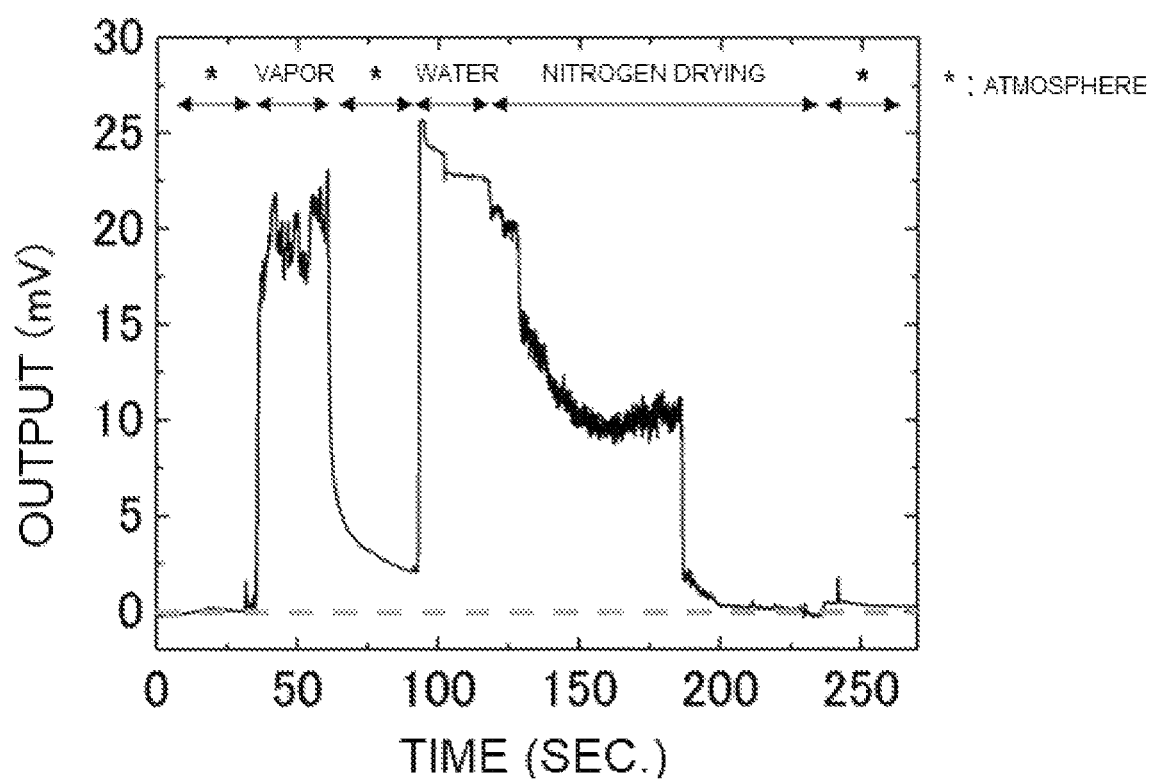
FIG. 2 is a graph showing a sensor signal measured when acetic acid vapor is exposed to the MSS, which is coated with a sensitive membrane that is durable against the liquid water and has high affinity for acetic acid, and then the MSS is immersed in the liquid water, is dried in nitrogen, and remains in the atmosphere, thereby being restored to a steady-state.
Figure 3:
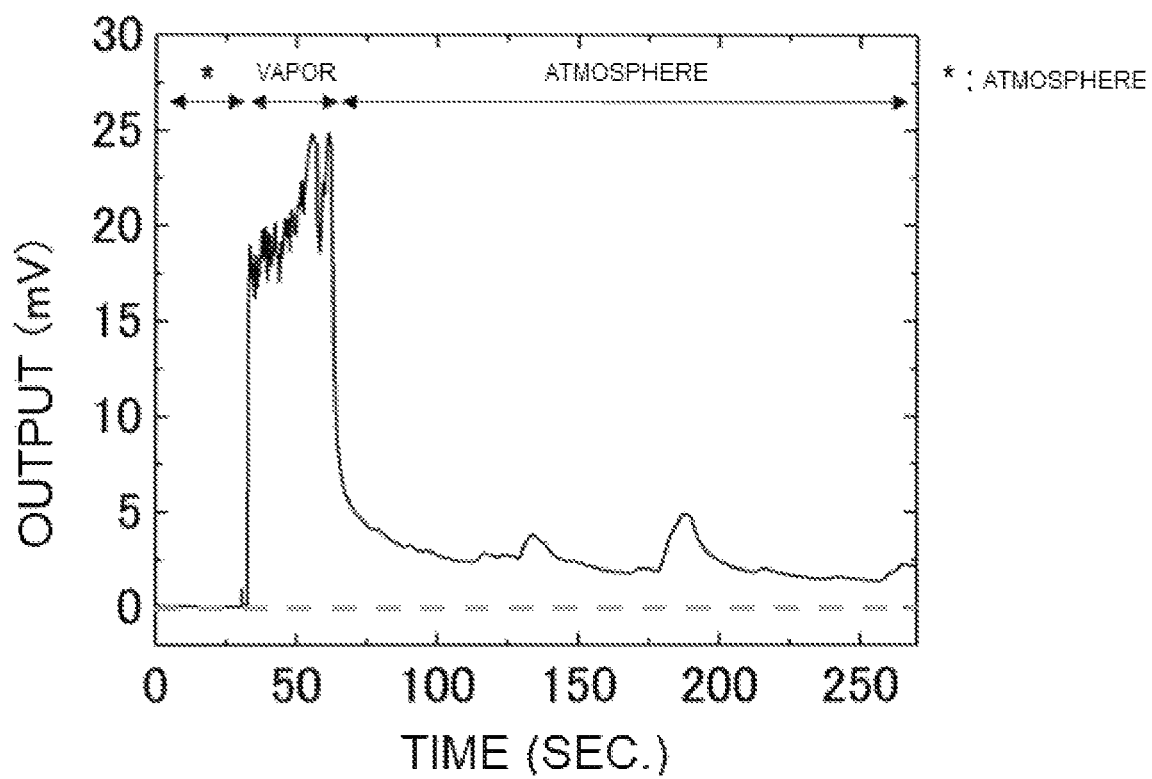
FIG. 3 is a graph showing a sensor signal measured when acetic acid vapor is exposed to the MSS, which is coated with a sensitive membrane that is durable against the liquid water and has high affinity for acetic acid, and then the MSS remains in the atmosphere without being immersed in the liquid water.

Hereinafter, an embodiment of a gas sensor device and a method for removing a gas component of the invention will be described.

The gas sensor device of the invention comprises a gas sensor equipped with a sensor main body and a sensitive membrane and cleaning means.

The sensor main body that configures the gas sensor is not particularly limited as long as the sensor main body is capable of detecting characteristic parameters indicating various characteristics of a component present in a gas phase or a liquid phase, such as a characteristic parameter of the component.

For example, a characteristic parameter that is detected by the sensor main body may be one or more of surface stress, stress, force, surface tension, pressure, mass, elasticity, Young's modulus, Poisson ratio, resonance frequency, frequency, volume, thickness, viscosity, density, magnetic force, magnetic quantity, magnetic field, magnetic flux, magnetic flux density, electric resistance, electric quantity, permittivity, electric power, electric field, electric charge, current, voltage, potential, mobility, electrostatic energy, capacitance, inductance, reactance, susceptance, admittance, impedance, conductance, plasmon, refractive index, intensity, temperature, and the like.

As the sensor main body, it is possible to appropriately employ a known sensor that is capable of detecting the various characteristic parameters described above.

Specifically, it is possible to exemplify the sensor main body with various types of surface stress sensors described in Patent Literature 2, an oscillator such as a quartz crystal microbalance or a cantilever, a surface plasmon resonance (SPR), a field-effect transistor, a capacitance reading sensor, or the like; however, a shape, a material, a size, or the like thereof is not particularly limited. For example, it is possible to exemplify the sensor main body with preferably a thin member supported at one position or a plurality of positions. Additionally, it is possible to employ an object having various embodiments, such as a thin body, a thin object supported at two positions, such as a both-side supported beam, or at more positions, or the like, for example.

The sensitive membrane is coated on a surface of the sensor main body and has responsiveness to a gas and is durable against a liquid to be described below.

The "durability" against liquid as used herein means a property of a substance that can maintain substantially the same characteristic as the characteristic observed before the substance is brought into contact with the liquid without irreversibly changing the practical characteristic such as deforming when the substance is brought into contact with or approaches the liquid by being immersed in the liquid or dissolving in the liquid.

A material of the sensitive membrane durable against the liquid is not specifically limited. Specifically, it is preferable that the sensitive membrane is formed with an elemental substance such as metal, a compound such as an oxide or a sulfide, a polymer, an inorganic-organic hybrid, fine particles made of a biomaterial such as protein, and a substance obtained by chemically modifying surfaces of the fine particles with a functional group, for example.

In this case, the fine particles that form the sensitive membrane may be bonded to a surface of the sensor main body by any interactions, thereby, not being easily desorbed from the surface of the sensor main body.

A grain size of the fine particles that form the sensitive membrane is not particularly limited; however, it is possible to exemplify the grain size with preferably a range of 1 nm to 1 mm, for example. More specifically, the grain size of the fine particles that form the sensitive membrane is preferably 100 μm or smaller, more preferably 1 μm or smaller, and still more preferably 100 nm or smaller.

In addition, the fine particles may have a dense structure, a sparse structure such as a porous or hollow structure, a core shell structure, or the like.

Further, in order to improve the durability of the sensitive membrane against the liquid, it is possible to add binders that improve cohesiveness between the fine particles or adhesiveness to the sensor main body, or a component other than the binders, in addition to the fine particles. In addition, the surface of the sensor main body is coated with a self-assembled membrane, and thus an affinity with the fine particles is enhanced. In this manner, it is possible to enhance the adhesiveness of the fine particles to the surface of the sensor main body via the self-assembled membrane.

Means for coating the surface of the sensor main body with the sensitive membrane can be exemplified with dip coating, spray coating, ink jet spotting, spin coating, casting, coating using a doctor blade or a dispenser, or the like, and the means is not particularly limited.

In addition, the sensitive membrane may be formed with a polymer of any structure as a main component, including the polymer having any structure of polyvinylpyrrolidone, polymethylmethacrylate, polyethyleneglycol, or the like.

The cleaning means contains a liquid for cleaning the gas sensor (the sensor main body and the sensitive membrane).

As the liquid, for example, it is possible to use water, ethanol, acetone, isopropyl alcohol, formaldehyde (formalin), acetic acid, methyl ethyl ketone (2-butanone), methanol, 1-butanol, 1-pentanol, n-hexane, n-heptane, n-octane, n-nonane, n-decane, n-undecane, n-dodecane, benzene, toluene, xylene (o-, m-, p-, or a mixture thereof), 1,2-dichlorobenzene, 1,3-dichlorobenzene, N,N-dimethylformamide, hydrochloric acid, sulfuric acid, nitric acid, carbonated water, sodium hydroxide solution, sodium hypochlorite solution, surfactant solution, or a liquid obtained by arbitrarily mixing any substances described above.

In addition, from the various liquids, it is possible to appropriately select a liquid having high solubility with respect to an analyte gas component (component adsorbed to the gas sensor), with the durable material of the sensitive membrane selected as appropriate depending on the types of those liquids.

The cleaning means may be capable of cleaning the gas sensor (the sensor main body and the sensitive membrane), and it is possible to employ various embodiments of the cleaning means.

Figure 4:
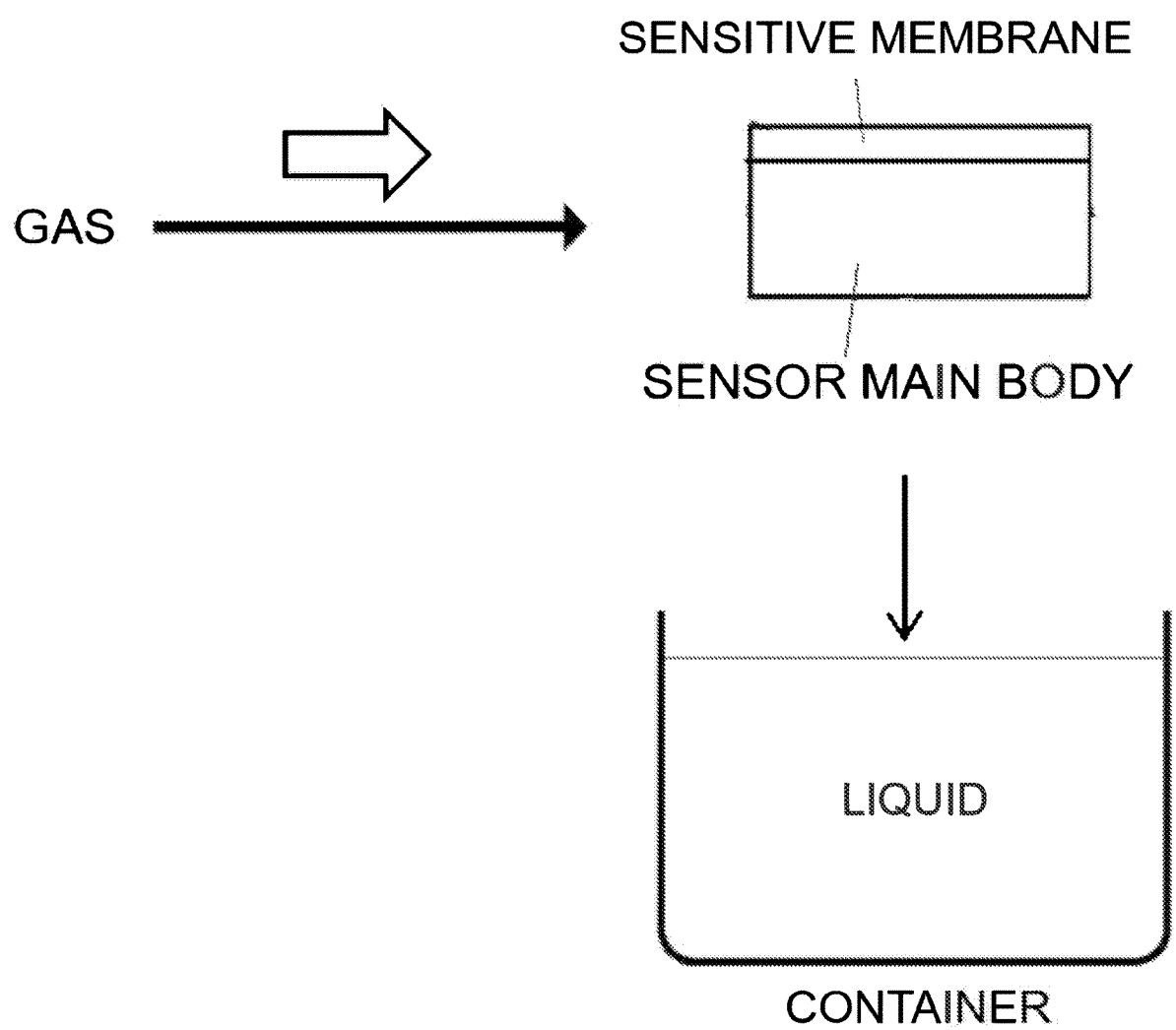
FIG. 4 shows an embodiment of the gas sensor device.

Specifically, as an embodiment of the cleaning means shown in FIG. 4, a container (a beaker, a well plate, or the like) which holds the liquid inside and in which it is possible to immerse the gas sensor in the liquid can be exemplified, for example. The gas sensor is immersed in the liquid, and thereby it is possible to clean the gas sensor.

Figure 5:
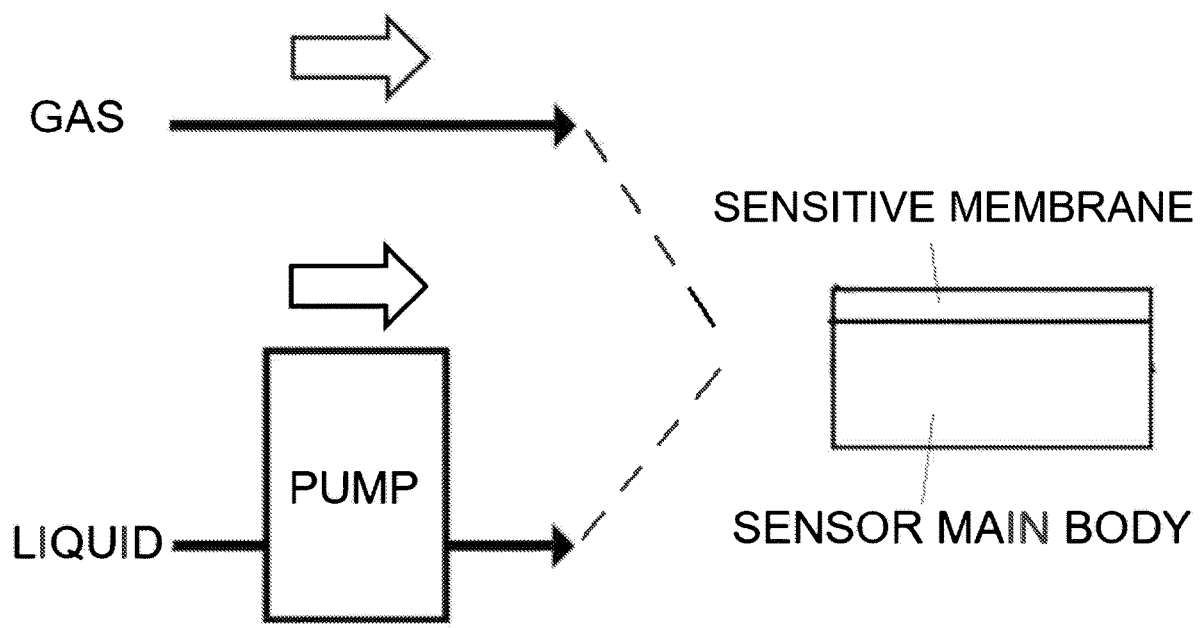
FIG. 5 shows another embodiment of the gas sensor device.

In addition, as another embodiment of the cleaning means shown in FIG. 5, an embodiment can be exemplified, in which liquid supply means such as a pump and a chamber, in which the gas sensor is installed, are connected via a flow channel. In the embodiment, the liquid is supplied into the chamber by the liquid supply means, and thereby the gas sensor and the liquid to be brought into contact with each other such that cleaning is performed.

In this manner, the gas sensor device of the invention includes the gas sensor having the sensitive membrane that has durability against the liquid and the cleaning means for cleaning the gas sensor (the sensor main body and the sensitive membrane). Hence, the gas sensor is immersed in the liquid by the cleaning means, or the liquid is supplied to the gas sensor. In this manner, it is possible to clean the gas sensor. Consequently, since it is possible to remove a component adsorbed on the gas sensor, and it is possible to restore a signal baseline of the gas sensor to a constant state, it is possible to reliably secure reproducibility of a measurement result.

Next, an embodiment of the method for removing a gas component of the invention will be described. The description common to the content described above as the embodiment of the gas sensor device of the invention is partially omitted.

The method for removing a gas component of the invention is a method of removing a gas component adsorbed on the gas sensor described above with the liquid. As described above, the gas sensor includes the sensor main body, which is capable of detecting a characteristic parameter of a component present in a gas phase or a liquid phase, and the sensitive membrane, which is coated on the surface of the sensor main body and is durable against the liquid.

Here, the "gas component adsorbed on the gas sensor" means an analyte component derived from a gas that is detected by being adsorbed on the sensitive membrane of the gas sensor.

The method for removing a gas component of the invention includes:

(1) a cleaning step of causing the gas sensor and the liquid to be brought into contact with each other; and (2) a drying step of drying the gas sensor in a gas phase after the cleaning step.

Hereinafter, the steps will be described.

In the cleaning step, the gas sensor and the liquid are brought into contact with each other. As described above, since the sensitive membrane is formed with the material durable against the liquid used in the cleaning step, the gas sensor and the liquid can be brought into contact with each other.

For example, it is possible to exemplify a cleaning method of the gas sensor in the cleaning step with a method of immersing (coming into contact with) the gas sensor for a predetermined time in the liquid held in the container (a beaker, a well plate, or the like) or a method of causing the gas sensor and the liquid to be brought into contact with each other by supplying the liquid to the gas sensor by the liquid supply means such as a pump. In addition, the gas sensor and a plurality of liquids can be brought into contact with each other in order, or the gas sensor and one type of liquid can be brought into contact with each other and, then, another type of liquid is added to the liquid, for example. Further, a characteristic such as a concentration or a temperature of the liquid that is brought into contact with the gas sensor may be changed at a timing such as before the liquid is brought into contact with the gas sensor or while the liquid is brought into contact with the gas sensor. Depending on a case, a gas is introduced to the liquid that is in contact with the gas sensor and forms bubbles, and thereby it is possible to use a state in which a gas phase and a liquid phase are brought into contact with each other.

Further, as another method of the cleaning method of the gas sensor in the cleaning step, for example, a temperature of the gas sensor can be decreased, and thereby the gas sensor and the liquid can be brought into contact with each other such that the cleaning can be performed by using a state in which liquid vapor is condensed into dew on the surface of the sensitive membrane. The "dew condensation" in this case is not limited to a phenomenon involving water and water vapor but may be a phenomenon in which the liquid contained in the cleaning means and its vapor are involved.

Further, in the cleaning step, it is preferable that a reference value in a liquid phase state is calculated based on a signal value of a characteristic parameter of a component in a liquid phase, which is detected by the sensor.

Here, the reference value is described. Since humidity or the like is continuously fluctuated in the gas phase, the signal from the sensor main body is likely to be continuously unsteady. However, since a change in concentration or the like is relatively small in the liquid phase, the signal is likely to be stable. In this respect, the "reference value" is obtained in a state in which the signal is likely to be stable in the liquid phase, and this is positively used.

It is needless to say that, in a state in which the sensor is accommodated in a container or the like such that an air current is not disturbed, it is possible to stabilize the signal even in the gas phase. However, in the gas phase, in order to desorb the gas molecules adsorbed on the sensitive membrane and spread into the sensitive membrane, a relatively long time is likely to be taken. In addition, in the gas phase, it is more difficult to maintain an ambient gas environment in a constant condition than in a liquid phase. By comparison, when a chip of the sensor is put in the liquid phase, gas molecules in the sensitive membrane may dissolve into the liquid phase, and thus equilibrium tends to be achieved in a short time. In addition, it is easier to maintain a constant condition in the liquid phase by a simple operation such as "just immersing in water" than in the case of the gas phase. Since it is possible to easily reach a stable condition with good reproducibility in a short time based on such a situation described above, the signal value in the liquid phase is defined as the "reference value".

By comparison, in the gas phase in which it is necessary to provide a relatively large device such as a vacuum chamber, it takes a long time to achieve an equilibrium state, and thus it is difficult to reproduce the equilibrium state, an operation of maintaining a state for a while in practice until the signal is stabilized in the air is likely to be performed. Hence, the "reference value" indicating that the reproducibility is a prerequisite is not used, but the "convergence value" which does not indicate that the reproducibility is a prerequisite is used.

For example, in a case where the gas sensor and the liquid are continuously brought into contact with each other, the signal value depending on the component in the liquid phase is obtained by the sensor, and the signal value comes into a state in which variation with time is small. Hence, a constant value such as an average value is calculated from a range of the signal value, and the calculated value can be the reference value. It is needless to say that, as long as the signal value converges on a value within an error range in which no practical problem from the constant value arises in a short time during cleaning in the liquid phase, the converging constant value can be set as the reference value. Additionally, it is needless to say that a convergence time of the signal value significantly changes due to a composition or a thickness of the sensitive membrane, a type or an amount of adsorbed component, a type of liquid for the cleaning, a flow rate of the liquid in the vicinity of the sensitive membrane, or the like; however, the convergence time is about several seconds to tens of seconds in general.

In addition, in a case where the gas sensor and the liquid are intermittently brought into contact with each other at predetermined intervals, the signal value depending on the component or the measurement condition in the liquid phase is obtained by the sensor, for example, and the signal value is reproduced in a repeated pattern as the variation with time due to the contact with the liquid. Hence, a constant value is calculated from a range of the signal value, and the calculated value can be the reference value.

In this manner, in the invention, a state in which the constant value (reference value) of the signal depending on the component in the liquid phase is obtained by the sensor is referred to as a "liquid phase steady-state".

In the drying step, the gas sensor is dried in the gas phase after the cleaning step.

Specifically, it is possible to appropriately employ a method of exposing the gas sensor to the air, nitrogen gas, or the like or a method of placing and drying the gas sensor in the gas phase, for example. A type of gas used in the drying step, the component in the gas phase, or the like is not particularly limited; however, the gas can be exemplified preferably with an inert gas (for example, the nitrogen gas). In addition, it is also possible to appropriately set a drying time or the like in association with a state of the gas sensor.

In the drying step, the characteristic parameter of the component in the gas phase, which is detected by the sensor main body, has a signal that converges on a constant value depending on a component present in the gas phase, the measurement condition (temperature or humidity), or the like. The signal value (convergence value) that converges in the drying step is not defined as a specific value; however, it is desirable that the signal value is equal to the signal value (a value of an initial baseline) before the gas sensor and an analyte gas are brought into contact with each other, for example.

In this manner, in the invention, a state in which the convergence value of a constant signal depending on the component in the gas phase or the measurement condition, which is obtained by the sensor main body, is obtained is referred to as a "gas phase steady-state".

In the invention, it is possible to remove the component adsorbed on the gas sensor in the cleaning step, and the signal value obtained by the sensor is restored to the gas phase steady-state in the drying step. Therefore, since it is possible to restore the signal value which is the baseline of the gas sensor to a constant state (convergence value), it is possible to secure the reproducibility of the measurement result.

Thus, in a case where the reference value is calculated in the liquid phase state that is verified in the cleaning step, it is possible to adjust detection sensitivity of the sensor by comparing the reference value with the signal value (convergence value) of the gas phase steady-state.

Specifically, the liquid phase steady-state is unlikely to be influenced by fluctuation of the measurement condition or an environmental factor in the gas phase as described above, and the same condition is likely to be reproduced. Hence, in a case where a difference between the initially verified reference value and the signal value (convergence value) of the gas phase steady-state is significantly different from a difference between the reference value verified after a use and the signal value (convergence value) of the gas phase steady-state, as the gas sensor is repeatedly used, for example, it is found that there is a possibility that the sensor does not normally function. In this case, the embodiment is not limited thereto, and it is possible to adjust detection sensitivity, an offset (as an example, a change in baseline due to a change in balance of a bridge circuit that configures the sensor), or response signal (as an example, a series of variations with time of the sensor signal which occurs due to adsorption and desorption of a target to and from the sensor) of the sensor main body, for example. Specifically, any electric circuit condition for determining the sensor signal, such as a bridge voltage, a variable resistance value, or the like is appropriately adjusted, or a condition of a part such as a pump or a valve which is an element of a sensor system, the part flowing the sample, may be appropriately adjusted. In addition, in a stage of the next signal process, a process of adjusting the offset to the value before a use by subtracting the constant value from the entire signal, or applying any function to the sensor signal and adjusting rising or falling shape at a timing coincident with the timing in which the sample is adsorbed or desorbed, for example, such that the variation with time of the sensor signal observed in the cleaning step or the drying step of the sensor is approximate to the before the use. It is possible to further increase the reproducibility of the measurement result by the operation.

The gas sensor device and the method for removing a gas component of the invention are not limited to the embodiments described above, and it is possible to provide means for detecting the characteristic parameter of the component present in the gas phase and the liquid phase with higher accuracy, means for adjusting the measurement environment, a step, or the like, for example.

EXAMPLES

Hereinafter, the invention will be further described in detail with Examples; however, the invention is not limited to the following Examples.

<Example 1> Verification of restoration to gas phase/liquid phase steady-state by immersing sensor in liquid water, in a case where various types of vapors are exposed to sensor coated with sensitive membrane durable against liquid water.

The fine particles were synthesized on the basis of a method described in Non Patent Literature 3. The fine particles were synthesized by co-hydrolysis and condensation polymerization reaction of 3-aminopropyltriethoxysilane (APTES) and titanium tetraisopropoxide (TTIP) in an ammonia-based isopropanol (IPA) aqueous solution in which octadecylamine (ODA) is dissolved. Consequently, aminopropyl group-modified silica titania fine particles are obtained. The synthetic reaction was performed by using a Teflon (registered trademark) microreactor provided with a Y-shaped flow channel in micrometer size (Non Patent Literature 3). Precursor solutions were prepared as four solutions of a solution 1: APTES/IPA, a solution 2: $H_2O$/IPA/ammonia, a solution 3: TTIP/IPA, and a solution 4: $H_2O$/IPA and were prepared by adjusting volumes from a solution 1 to a solution 4 to the same volume. The precursor solutions were flowed simultaneously by a syringe pump at a constant speed. The solution 1 and the solution 2, and the solution 3 and solution 4 were mixed in the microreactors disposed side by side, respectively, discharged liquids from both reactors were further mixed in another microreactor, and thereby one reaction solution was obtained. The reaction solution was discharged to a precursor solution 5: ODA/H2O/IPA and was agitated at the constant speed to a discharge end. Then, the solution remained at room temperature, and fine particle dispersion liquid was obtained.

The Membrane-type Surface stress Sensor (MSS) was used as a sensor main body, and the fine particles were sprayed to the surface (on a sensor chip) of the sensor main body using a spray coater. In this manner, the sensitive membrane was formed on the surface of the sensor main body, and a gas sensor was obtained.

Subsequently, acetic acid vapor and isopropyl alcohol (IPA) vapor were exposed to the gas sensor. Specifically, a sample liquid was taken into a vial, and nitrogen flowed as a carrier gas, the nitrogen controlled by the mass flow controller at a flow rate of 100 mL/min. In this manner, the nitrogen gas containing a certain amount of the sample vapor accumulated in a headspace part of the vial was exposed to the gas sensor. Acquirement of the sample vapor was performed at room temperature.

For a certain time, the sensor, to which the sample vapor was exposed, was immersed in the liquid water so as to be cleaned (cleaning step), and the liquid phase steady-state was verified. Specifically, by using the same sensor holder as a sensor holder that was used in Patent Literature 2 (sensor holder), the sensor chip was inserted into a standard 96-well plate in which a constant amount of liquid water is filled, and the sensor was immersed in the liquid water. An operation of immersing the sensor in the 96-well plate was repeated three to four times, and the constant liquid phase steady-state was verified.

Then, the sensor was taken out from the 96-well plate, and the nitrogen gas was exposed. In this manner, the sensor was dried and remained in the atmosphere (drying step).

FIG. 1 shows a change in signal of the gas sensor, which is measured in the above series of operations.

When the series of operations was simply described, the sample vapor was exposed to the gas sensor remaining in the atmosphere, the gas sensor was immersed in the liquid water, then, nitrogen drying was performed, and the gas sensor remained again in the atmosphere.

As shown in FIG. 1, the gas sensor is immersed in water, and thereby restoration to the gas phase steady-state, in which the signal value observed before exposing the sample vapor is found, can be confirmed. Specifically, a signal output value of the gas sensor converges to a value approximate to 0 mV represented by a dashed line.

In addition, in a case where the gas sensor was immersed in the liquid water a plurality of times, restoration to the constant liquid phase steady-state with high reproducibility was verified in both cases of a case where the gas sensor was exposed to the acetic acid vapor and a case where the gas sensor was exposed to IPA vapor. Specifically, the signal output value of the gas sensor is restored to a value approximate to 23 mV represented by a dotted line. Additionally, when the gas sensor was immersed in the liquid water at the first time, a value obtained at the first time was confirmed to be different from the signal output values of the liquid phase steady-states measured from and after the second time. This is considered to be due to the following. The component of the sample vapor adsorbed on the gas sensor dissolves in water, the water becomes a solution of the sample vapor component, and thereby the water differs from pure water. This can be verified also from the following. In both cases of a case where the gas sensor is exposed to the acetic acid vapor and a case where the gas sensor is exposed to the IPA vapor, the gas sensor is immersed in the liquid water a plurality of times, and thereby an amount of sample vapor component adsorbed on the sensor is reduced. As the liquid water becomes closer to the pure water, the signal value also comes closer to a value in the liquid phase steady-state in the pure water.

From the result described above, in the gas sensor coated with the sensitive membrane composed of the fine particles durable against the liquid, the surface of the sensor was immersed in the liquid water, and thereby the liquid phase steady-state was achieved. Further, it was verified that it is possible to restore the state to the gas phase steady-state by the drying step.

On the other hand, in a case where the gas sensor was not immersed in the liquid water, the signal output value of the gas sensor was not restored to the gas phase steady-state, even when the gas sensor was placed in the atmosphere for about 400 seconds just after the vapor was exposed. <Example 2> Comparison of a case where operation for restoring steady-state is performed and a case where operation for restoring steady-state is not performed, regarding gas sensor coated with fine particles having high affinity with sample vapor.

The fine particle-coated MSS used in this example was prepared by the same method as that in <Example 1> described above. In addition, the operation for exposing the sample vapor was performed by the same method as that in <Example 1> described above.

(1) The series of operations of exposing the acetic acid vapor to the gas sensor prepared by coating the sensor main body with the aminopropyl group-modified silica titania fine particles used in Example 1, as the fine particles having a high affinity with acetic acid, then, immersing the gas sensor in the liquid water (cleaning step), and drying the gas sensor in nitrogen and leaving the gas sensor at the atmosphere (drying step) was performed.

FIG. 2 shows a change in signal of the gas sensor, which is detected by the operation. The sensitive membrane having the high affinity with acetic acid vapor was immersed in the liquid water (cleaning step) and dried (drying step), and thereby the signal value was also verified to be restored to the gas phase steady-state.

Additionally, since the dry nitrogen was exposed for a relatively short time in this example until water droplets were dried, similar process performed before the gas sensor is placed in the atmosphere is considered not to influence a restoring speed of the gas sensor placed in the atmosphere.

(2) In addition, as a comparative experiment, an operation was performed, in which the acetic acid vapor was exposed to the same gas sensor, and then the gas sensor remained in the atmosphere without immersing in the liquid water.

FIG. 3 shows a change in signal of the gas sensor, which is detected by the operation. In this case, it was verified that, even when the gas sensor remained in the atmosphere, the acetic acid vapor adsorbed once on the sensitive membrane having the affinity with the acetic acid was not simply desorbed and the signal value is not restored to the gas phase steady-state in a time range measured in this example.

(3) In addition, as another comparative experiment, an operation was performed, in which the acetic acid vapor was exposed to the same gas sensor, and then drying was performed by using nitrogen without immersion of the gas sensor in the liquid water. In this case, the same tendency of rather not restoring the signal value to the gas phase steady-state was also found. Also, from this result, it is possible to find that blowing of dry nitrogen has a small influence on the restoring speed.

(4) As described above, the following was verified. The sensitive membrane having a high affinity particularly with the sample vapor and water durability was used, the gas sensor and the liquid (water) were brought into contact with each other such that the cleaning was performed (cleaning step), the gas component adsorbed to the gas sensor was removed, the signal value converges on a substantially constant value (about 0 mV) in the drying step after the cleaning step, and the signal value was restored to the gas phase steady-state.

In examples described above, the experiment was conducted by using the aminopropyl group-modified particles as an example; however, the fine particles that can be used in the restoration to the steady-state is not limited to specific particles. For example, hydrophobic particles by appropriately selecting a functional group to be modified may be used.

INDUSTRIAL APPLICABILITY

As described above, according to the invention, in general, in regards to a gas sensor on which it is difficult to restore a state to a gas phase steady-state, excluding some sensors such as an oxide semiconductor-based gas sensor on which it is easy to perform cleaning and restoring by a high temperature operation or the like, it is possible to easily and effectively clean the gas sensor and restore the state of the sensor to the gas phase steady-state. In particular, a material having a certain level of durability against liquid is used in a sensitive membrane, and thereby it is possible to not only perform cleaning or restoring to the gas phase steady-state but also to adjust the gas sensor and increase reproducibility with reference to a reference value of a liquid phase steady-state that is a steady-state in the liquid.

Hence, the invention can be effectively applied to various fields of industries such as the medical industry, the environmental industry, the food industry, or the security industry in the future.

CITATION LIST

Patent Literature

Patent Literature 1: WO 2011/148774 A
Patent Literature 2: JP 2014-219223 A

Non Patent Literature

Non Patent Literature 1: D. Lee, S. Kim, I. Chae, S. Jeon, and T. Thundat, "Nanowell-patterned TiO2 microcantilevers for calorimetric chemical sensing," Applied Physics Letters 104, 141903 (2014).

Non Patent Literature 2: G. Yoshikawa, T. Akiyama, S. Gautsch, P. Vettiger, and H. Rohrer, "Nanomechanical Membrane-type Surface Stress Sensor," Nano Letters 11, 1044-1048 (2011).

Non Patent Literature 3: K. Shiba, T. Sugiyama, T. Takei, and G. Yoshikawa, "Controlled growth of silica-titania hybrid functional nanoparticles through a multistep microfluidic approach," Chem. Commun. 51, 15854-15857 (2015).

The invention claimed is:

1. A gas sensor device comprising:
a gas sensor; and
a cleaning means that contains a liquid for cleaning the gas sensor, the cleaning means being capable of cleaning the gas sensor with the liquid in a liquid state so that a gas component adsorbed on the gas sensor dissolves in the liquid,
wherein the gas sensor includes:
a sensor main body capable of detecting a characteristic parameter of a component present in a gas phase; and
a sensitive membrane that is coated on a surface of the sensor main body and is durable against the liquid.

2. The gas sensor device according to claim 1,
wherein the sensitive membrane is composed of fine particles having a grain size of 1 nm to 1 mm.

3. The gas sensor device according to claim 1,
wherein the cleaning means comprises:
(a) a means for immersing the gas sensor in the liquid in a container; or
(b) a liquid supply means that is capable of bringing the liquid into contact with the gas sensor.

4. A method for removing a gas component adsorbed on a gas sensor with a liquid,
wherein the gas sensor comprises:
a sensor main body that is capable of detecting a characteristic parameter of a component present in a gas phase; and
a sensitive membrane that is coated on a surface of the sensor main body and is durable against the liquid,
the method comprising:
(1) a cleaning step of causing the gas sensor and the liquid, which is in a liquid state, to be brought into contact with each other so that the gas component adsorbed on the gas sensor dissolves in the liquid; and
(2) a drying step of drying the gas sensor in a gas phase after the cleaning step.

5. The method for removing a gas component according to claim 4,
wherein, in (2) the drying step, a signal of a characteristic parameter detected by the sensor due to a component in the gas phase restores to a value before the gas sensor and an analyte gas were brought into contact with each other.

6. The method for removing a gas component according to claim 4,
wherein:
(a) the gas sensor is immersed in the liquid in a container; or
(b) the liquid is contacted with the gas sensor via a liquid supply means.

\* \* \* \* \*